US011065230B2

(12) United States Patent
Hermine et al.

(10) Patent No.: US 11,065,230 B2
(45) Date of Patent: Jul. 20, 2021

(54) METHODS AND PHARMACEUTICAL COMPOSITIONS FOR THE TREATMENT OF SYSTEMIC MASTOCYTOSIS (71) Applicants: INSERM (INSTITUT NATIONAL DE LA SANTE ET DE LA RECHERCHE MEDICALE), Paris (FR); FONDATION IMAGINE, Paris (FR); UNIVERSITE PARIS DESCARTES, Paris (FR); ASSISTANCE PUBLIQUE-HOPITAUX DE PARIS (APHP), Paris (FR); CENTRE NATIONAL DE LA RECHERCHE SCIENTIFIQUE (CNRS), Paris (FR); UNIVERSITE DE CAEN NORMANDIE, Caen (FR); CENTRE HOSPITALIER REGIONAL UNIVERSITAIRE DE CAEN, Caen (FR)

(72) Inventors: Olivier Hermine, Paris (FR); Flavia Guillem, Paris (FR); Gandhi Damaj, Paris (FR); Sophia Ladraa, Paris (FR)

(73) Assignees: INSERM (INSTITUT NATIONAL DE LA SANTE ET DE LA RECHERCHE MEDICALE), Paris (FR); FONDATION IMAGINE, Paris (FR); UNIVERSITE PARIS DESCARTES, Paris (FR); ASSISTANCE PUBLIQUE—HOPITAUX DE PARIS (APHP), Paris (FR); CENTRE NATIONAL DE LA RECHERCHE SCIENTIFIQUE (CNRS), Paris (FR); UNIVERSITE DE CAEN NORMANDIE, Caen (FR); CENTRE HOSPITALIER REGIONAL UNIVERSITAIRE DE CAEN, Caen (FR)

( * ) Notice: Subject to any disclaimer, the term of this patent is extended or adjusted under 35 U.S.C. 154(b) by 0 days.

(21) Appl. No.: 16/330,956

(22) PCT Filed: Sep. 15, 2017

(86) PCT No.: PCT/EP2017/073234
§ 371 (c)(1),
(2) Date: Mar. 6, 2019

(87) PCT Pub. No.: WO2018/050801
PCT Pub. Date: Mar. 22, 2018

(65) Prior Publication Data
US 2019/0247416 A1    Aug. 15, 2019

(30) Foreign Application Priority Data

Sep. 16, 2016 (EP) ................... 16306181

(51) Int. Cl.
*A61K 31/4196* (2006.01)
*A61P 37/00* (2006.01)
(Continued)

(52) U.S. Cl.
CPC ........ *A61K 31/4196* (2013.01); *A61K 31/397* (2013.01); *A61K 31/4245* (2013.01); *A61K 31/506* (2013.01); *A61P 37/00* (2018.01); *A61K 31/497* (2013.01); *A61K 31/7105* (2013.01); *A61P 35/04* (2018.01); *C12N 2310/14* (2013.01); *C12N 2310/531* (2013.01)

(58) Field of Classification Search
CPC .............. A61K 31/4196; A61K 31/506; A61K 31/397; A61K 31/4245; A61P 37/00
See application file for complete search history.

(56) References Cited

U.S. PATENT DOCUMENTS

| 2008/0176879 A1* | 7/2008 | Alland | A61K 31/506 |
| | | | 514/275 |
| 2013/0046009 A1 | 2/2013 | Kapur | |
| 2014/0147415 A1* | 5/2014 | Moussy | A61K 31/155 |
| | | | 424/85.7 |

FOREIGN PATENT DOCUMENTS

| WO | 2009/071680 A2 | 6/2009 |
| WO | 2012/099807 A1 | 7/2012 |

(Continued)

OTHER PUBLICATIONS

London et al: "Preclinical Evaluation of the Novel, Orally Bioavailable Selective Inhibitor of Nuclear Export (SINE) KPT-335 in Spontaneous Canine Cancer: Results of a Phase I Study", PLOS ONE, vol. 9, No. 2, pp. 1-11, Feb. 4, 2014.

*Primary Examiner* — Theodore R. Howell
(74) *Attorney, Agent, or Firm* — W&C IP (57) ABSTRACT The present invention relates to methods and pharmaceutical compositions for the treatment of systemic mastocytosis. The inventors showed the effect of KPT-251 treatment on SCF-dependent human Mast cell (MC) line without KIT mutation (WT ROSA) and on two factor-independent MC lines with KIT mutations : ROSA Δ 417-419 insY and ROSA D816V. KPT is a Selective Inhibitor of Nuclear Export (SINE) that specifically inhibits the activity of the exportin-1 (XPO1). KPT-251 treatment induces minimal toxicity in non-cancerous hematopoietic cells both in vitro and in vivo. In particular, the present invention relates a method of treating systemic mastocytosis in patient in need thereof comprising administering to the patient a therapeutically effective amount of a XPO1 inhibitor.

4 Claims, 4 Drawing Sheets (51) Int. Cl.
*A61K 31/506* (2006.01)
*A61K 31/397* (2006.01)
*A61K 31/4245* (2006.01)
A61K 31/7105 (2006.01)
A61P 35/04 (2006.01)
A61K 31/497 (2006.01)

(56) References Cited

FOREIGN PATENT DOCUMENTS

| | | |
|---|---|---|
| WO | 2014/205393 A1 | 12/2014 |
| WO | 2016/008433 A1 | 1/2016 |

* cited by examiner

METHODS AND PHARMACEUTICAL COMPOSITIONS FOR THE TREATMENT OF SYSTEMIC MASTOCYTOSIS

FIELD OF THE INVENTION

The present invention relates to methods and pharmaceutical compositions for the treatment of systemic mastocytosis.

BACKGROUND OF THE INVENTION

Mastocytosis is a disease characterized by the pathologic proliferation and accumulation of abnormal mast cells in one or more tissues. There are two forms of mastocytosis: cutaneous mastocytosis (CM) and systemic mastocytosis (SM). In SM, mastocytes accumulate in one or more extracutaneous tissuss. SM represents 10% of mast cell disease and the majority (80%) of SM present the gain-of-function D816V mutation of the tyrosine kinase receptor KIT inducing constitutive activation of KIT signaling independently of SCF activation. This mutation results in increased production of mast cells and accumulation in extracutaneous organs that might results in organ failure (bone marrow, lymph nodes, liver, gastointestinal tract, spleen). Unfortunately, activating D816V KIT mutation is known to be associated with resistance to the currently available tyrosine kinase inhibitor (TKI) treatment for SM, approved by FDA: Imatinib. New efficient therapeutics are thus a priority for the treatment of SM with D816V mutation.

SUMMARY OF THE INVENTION

The present invention relates to methods and pharmaceutical compositions for the treatment of systemic mastocytosis. In particular, the present invention is defined by the claims.

DETAILED DESCRIPTION OF THE INVENTION

The present invention relates a method of treating systemic mastocytosis in patient in need thereof comprising administering to the patient a therapeutically effective amount of a XPO1 inhibitor.

As used herein, the term "mastocytosis", relates to systemic mastocytosis, for example mastocytoma, and also to canine mast cell neoplasms. Mastocytosis is a myeloproliferative disorder with limited treatment options and generally a poor prognosis. The pathogenesis of mastocytosis has been attributed to constitutive activation of the receptor tyrosine kinase KIT. In a large majority of mastocytosis patients, the deregulated tyrosine kinase activity of KIT is due to a mutation within the amino acid 816 of the protein (D816V) which also confers resistance to imatinib or imatinib mesylate in vitro and in vivo.

As used herein, the term "systemic mastocytosis" or "SM" encompasses the 4 categories of SM defined by the World Health Organization according to their location and aggressiveness: indolent SM (ISM), SM with associated clonal hematologic non-MC disease, aggressive SM (ASM), and MC leukemia (MCL). The prognosis of patients with ASM and MCL is poor due to an aggressive nature of the cells and their tendency to detach from the main tumor. Many of these tumors carry mutations in the tyrosine kinase receptor: KIT (stem cell factor receptor) that renders it constitutively activated leading to uncontrolled growth of the malignant MCs. Clinical presentation in adult SM is heterogenous and includes skin disease (usually urticaria pigmentosa), mast cell mediator-release symptoms (headache, flushing, lightheadedness, syncope, anaphylaxis, etc), and direct or indirect organ damage (bone pain from lytic bone lesions, osteoporosis or bone fractures, hepatosplenomegaly, cytopenia from bone marrow involvement). In addition, around 20% of patients with SM may display significant and sometimes isolated blood eosinophilia.

In particular, the method of the present invention is particularly suitable for the treatment of patients harbouring the KIT mutation D816V or Delta 417-419 insY. The term "KIT" has its general meaning in the art and refers to the human KIT. KIT is also known as "kit", "c-kit", "CD117" or "stem cell factor receptor". An exemplary native KIT amino acid sequence is provided in the UniProtKB/Swiss-Prot under accession number P10721). Methods of detecting KIT mutations are well known in the art and typically involves PCR assays.

As used herein, the term "treatment" or "treat" refer to both prophylactic or preventive treatment as well as curative or disease modifying treatment, including treatment of patient at risk of contracting the disease or suspected to have contracted the disease as well as patients who are ill or have been diagnosed as suffering from a disease or medical condition, and includes suppression of clinical relapse. The treatment may be administered to a patient having a medical disorder or who ultimately may acquire the disorder, in order to prevent, cure, delay the onset of, reduce the severity of, or ameliorate one or more symptoms of a disorder or recurring disorder, or in order to prolong the survival of a patient beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a patient during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a patient during treatment of an illness, e.g., to keep the patient in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., pain, disease manifestation, etc.]).

As used herein the term "XPO1" has its general meaning in the art and refers to the exportin 1 protein. The protein mediates leucine-rich nuclear export signal (NES)-dependent protein transport. The protein is also called Chromosomal Region Maintenance 1 (Crm1).

As used herein the term "XPO1 inhibitor" designates any compound or treatment that reduces or blocks the activity of XPO1. The term also includes inhibitors of XPO1 expression.

XPO1 inhibitors are well known in the art. In certain embodiments of the invention the XPO1 inhibitor is selected from small molecule compounds that have been disclosed in the following publications WO2011109799, WO2012099807, WO2013020024, WO 2013019548, and WO2013019561.

In some embodiments, the XPO1 inhibitor is selected from the group consisting of the following compounds:

and pharmaceutically acceptable salts thereof.

In some embodiments, the XPO1 inhibitor is selected from the group consisting of (Z)-3-[3-(3-Chloro-phenyl)-[1,2,4]-triazol-1-yl]-acrylic acid ethyl ester; (E)-3-[3-(3-Chloro-phenyl)-[1,2,4]-triazol-1-yl]-acrylic acid ethyl ester; (Z)-3-[3-(3-Chloro-phenyl)-[1,2,4]-triazol-1-yl]-acrylic acid isopropyl ester; (E)-3-[3-(3-Chloro-phenyl)-[1,2,4]-triazol-1-yl]-acrylic acid isopropyl ester; (Z)-3-[3-(3-Chloro-phenyl)-[1,2,4]-triazol-1-yl]-acrylic acid tert-butyl ester; (Z)-3-[3-(3-Chloro-phenyl)-[1,2,4]-triazol-1-yl]-acrylic acid tert-butyl ester; (E)-3-[3-(3-Chloro-phenyl)-[1,2,4]-triazol-1-yl]-N-phenyl-acryl amide; (E)-N-(2-Chloro-phenyl)-3-[3-(3-chloro-phenyl)-[1,2,4]-triazol-1-yl]-acryl amide; (4-{(E)-3-[3-(3-Chloro-phenyl)-[1,2,4]-triazol-1-yl]-acryloylamino}-phenyl)-carbamic acid tert-butyl ester; (E)-3-[3-(3-Chloro-phenyl)-[1,2,4]-triazol-1-yl]-N-(4-methoxy-phenyl)-acryl amide; (E)-3-[3-(3-Chloro-phenyl)-[1,2,4]-triazol-1-yl]-N-methyl-N-phenyl-acryl amide; (E)-3-[3-(3-Chloro-phenyl)-[1,2,4]-triazol-1-yl]-N-methyl-N-phenyl-acryl amide; (E)-N-(4-Amino-phenyl)-3-[3-(3-chloro-phenyl)-[1,2,4]-triazol-1-yl]-acryl amide and/or a pharmaceutically-acceptable salt thereof.

In some embodiments, the XPO1 inhibitor is selected from the group consisting of the following compounds:

I-1

I-2

I-3

I-4

I-5

I-6

I-7

I-8

I-9 or a pharmaceutically acceptable salt thereof.

In some embodiments, the XPO1 inhibitor is selected from the group consisting of a compound selected from the group consisting of 1-(4-methoxyphenyl)-1H-pyrrole-2,5- dione; 1-(4-bromo-2,5-difluorophenyl)-1H-pyrrole-2,5-dione; 3-methyl-1-(1-methyl-1H-pyrazol-3-yl)-1H-pyrrole-2,5-dione; 4-(2,5-dioxo-2,5-dihydro-1H-pyrrol-1-yl)-N-(5-methylisoxazol-3-yl)benzenesulfonamide; 1-(3-benzoyl-4-methylthiophen-2-yl)-1H-pyrrole-2,5-dione; 1-(4-(3-(trifluoromethyl)-1H-pyrazol-1-yl)phenyl)-1H-pyrrole-2,5-dione; 1-(4-(4-chlorophenyl)thiazol-2-yl)-3-methyl-1H-pyrrole-2,5-dione; 1-(benzo [b]thiophen-3-ylmethyl)-1H-pyrrole-2,5-dione; 1-(3,4-dimethoxyphenethyl)-1H-pyrrole-2,5-dione; 1-(naphthalen-1-yl)-1H-pyrrole-2,5-dione; 1-(4-cyclohexylphenyl)-1H-pyrrole-2,5-dione; 1-(2-benzoylphenyl)-1H-pyrrole-2,5-dione; 1-(4-morpholinophenyl)-1H-pyrrole-2,5-dione; 1-(4-chlorophenethyl)-1H-pyrrole-2,5-dione; 1-(2-(thiophen-2-yl)ethyl)-1H-pyrrole-2,5-dione; 1-([3,4]methylenedioxybenzyl)-1H-pyrrole-2,5-dione amide and/or a pharmaceutically-acceptable salt thereof.

In some embodiments, the XPO1 inhibitor is selected from the group consisting of the following compounds:

I-7

I-8

I-3

I-9, I-10

I-4

I-5

I-11

I-6

I-12

I-13

I-14

I-15

I-16

I-17

I-18

I-19

I-20

I-21

I-22

I-23

I-25 or I-26.

In some embodiments, the XPO1 inhibitor is KPT-330 (Etchin J, Sanda T, Mansour M R, Kentsis A, Montero J, Le B T, Christie A L, McCauley D, Rodig S J, Kauffman M, Shacham S, Stone R, Letai A, Kung A L, Thomas Look A. KPT-330 inhibitor of CRM1 (XPO1)-mediated nuclear export has selective anti-leukaemic activity in preclinical models of T-cell acute lymphoblastic leukaemia and acute myeloid leukaemia. Br J Haematol. 2013 Apr;161(1):117-27. doi: 10.1111/bjh.12231. Epub 2013 Feb 4).

KPT-330

In some embodiments, the XPO1 inhibitor is KPT-276 (Schmidt J, Braggio E, Kortuem K M, Egan J B, Zhu Y X, Xin C S, Tiedemann R E, Palmer S E, Garbitt V M, McCauley D, Kauffman M, Shacham S, Chesi M, Bergsagel P L, Stewart A K. Genome-wide studies in multiple myeloma identify XPO1/CRM1 as a critical target validated using the selective nuclear export inhibitor KPT-276. Leukemia. 2013 Jun 11. doi: 10.1038/leu.2013.172.).

KPT-276

In some embodiments, the XPO1 inhibitor is KPT-251 ((Z)-2-(2-(3-(3,5-bis(trifluoromethyl)phenyl)-1H-1,2,4-triazol-1-yl)vinyl)-1,3,4-oxadiazol).

In some embodiments, the inhibitor is a short hairpin RNA (shRNA), a small interfering RNA (siRNA) or an antisense oligonucleotide which inhibits the expression of XPO1. A short hairpin RNA (shRNA) is a sequence of RNA that makes a tight hairpin turn that can be used to silence gene expression via RNA interference. shRNA is generally expressed using a vector introduced into cells, wherein the vector utilizes the U6 promoter to ensure that the shRNA is always expressed. This vector is usually passed on to daughter cells, allowing the gene silencing to be inherited. The shRNA hairpin structure is cleaved by the cellular machinery into siRNA, which is then bound to the RNA-induced silencing complex (RISC). This complex binds to and cleaves mRNAs that match the siRNA to which it is bound. Small interfering RNA (siRNA), sometimes known as short interfering RNA or silencing RNA, are a class of 20-25 nucleotide-long double- stranded RNA molecules that play a variety of roles in biology. Most notably, siRNA is involved in the RNA interference (RNAi) pathway whereby the siRNA interferes with the expression of a specific gene. Anti-sense oligonucleotides include anti-sense RNA molecules and anti-sense DNA molecules, would act to directly block the translation of the targeted mRNA by binding thereto and thus preventing protein translation or increasing mRNA degradation, thus decreasing the level of the targeted protein, and thus activity, in a cell. For example, antisense oligonucleotides of at least about 15 bases and complementary to unique regions of the mRNA transcript sequence can be synthesized, e.g., by conventional phosphodiester techniques. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732). Antisense oligonucleotides, siRNAs, shRNAs of the invention may be delivered in vivo alone or in association with a vector. In its broadest sense, a "vector" is any vehicle capable of facilitating the transfer of the antisense oligonucleotide, siRNA, shRNA or ribozyme nucleic acid to the cells and typically mast cells. Typically, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the antisense oligonucleotide, siRNA, shRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rous sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

By a "therapeutically effective amount" of the XPO1 inhibitor of the invention as above described is meant a sufficient amount of the compound. It will be understood, however, that the total daily usage of the compounds and compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidential with the specific polypeptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

The XPO1 inhibitor of the invention may be combined with pharmaceutically acceptable excipients, and optionally sustained-release matrices, such as biodegradable polymers, to form therapeutic compositions. "Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type. In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms. Galenic adaptations may be done for specific delivery in the small intestine or colon. Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. The pharmaceutical forms suitable for injectable use include sterile aqueous solutions or dispersions; formulations including sesame oil, peanut oil or aqueous propylene glycol ; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. Solutions comprising XPO1 inhibitors of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms. The XPO1 inhibitor of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifusoluble agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin. Sterile injectable solutions are prepared by incorporating the active polypeptides in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject. The XPO1 inhibitor of the invention may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered. In addition to the XPO1 inhibitors of the invention formulated for parenteral administration, such as intravenous or intramuscular injection, other pharmaceutically acceptable forms include, e.g. tablets or other solids for oral administration; liposomal formulations ; time release capsules ; and any other form currently used.

The invention will be further illustrated by the following figures and examples. However, these examples and figures should not be interpreted in any way as limiting the scope of the present invention.

EXAMPLE

Mastocytosis is a disease characterized by the pathologic proliferation and accumulation of abnormal mast cells in one or more tissues. There are two forms of mastocytosis : cutaneous mastocytosis (CM) and systemic mastocytosis (SM). In SM, mastocytes accumulate in one or more extracutaneous tissus. SM represents 10% of mast cell disease and the majority (80%) of SM present the gain-of-function D816V mutation of the tyrosine kinase receptor KIT inducing constitutive activation of KIT signaling independently of activation by its ligand SCF. This mutation results in increased production of mast cells and accumulation in extracutaneous organs that might results in organ failure (bone marrow, lymph nodes, liver, gastointestinal tract, spleen). Unfortunately, activating D816V KIT mutation is known to be associated with resistance to the currently available tyrosine kinase inhibitor (TKI) treatment for SM, approved by FDA : Imatinib. New efficient therapeutics are thus a priority for the treatment of SM with D816V mutation.

Here we show the effect of KPT-251 treatment on two different human mast cell (MC) lines : ROSA and HMC1 cell lines and on bone marrow cells depleted with erythrocytes, from a patient with aggressive mastocytosis with D816V mutation. ROSA cell lines include a SCF-dependent MC line without KIT mutation (ROSA WT) and a factor-independent MC line with KIT mutation D816V (ROSA D816V). HMC1 factor-independent MC lines include HMC1.1 with G560V KIT mutation and HMC1.2 with G560V and D816V KIT mutation. KPT-251 is a Selective Inhibitor of Nuclear Export (SINE) that specifically inhibits the activity of the exportin-1 (XPO1). KPT-251 treatment induces minimal toxicity in non-cancerous hematopoietic cells both in vitro and in vivo'.

Human MC lines ROSA WT and ROSA D816V were treated for 72 hours with KPT-251 at 100 nM, 1000 nM, or with DMSO (control) and HMC1.1 and HMC1.2 were treated for 72 hours with KPT-251 at 100 nM, 500 nM, 1000 nM, or with DMSO (control). WT ROSA cell lines were cultured in the presence of human SCF at 100 ng/mL. Cells were plated at 0,5 million/mL at day 0. Cell death percentage was assessed by counting after trypan blue staining or Annexin V labelling analysed by flow cytometry. Proliferation was assessed by counting after trypan blue staining. Bone marrow cells from patient were depleted with erythrocytes and then treated for 7 days with KPT at 100 nm, 500 nM, 1000 nm, or with DMSO (control) in culture media supplemented with SCF at 80 ng/mL and IL6 at 50 ng/mL.

Figure 1:
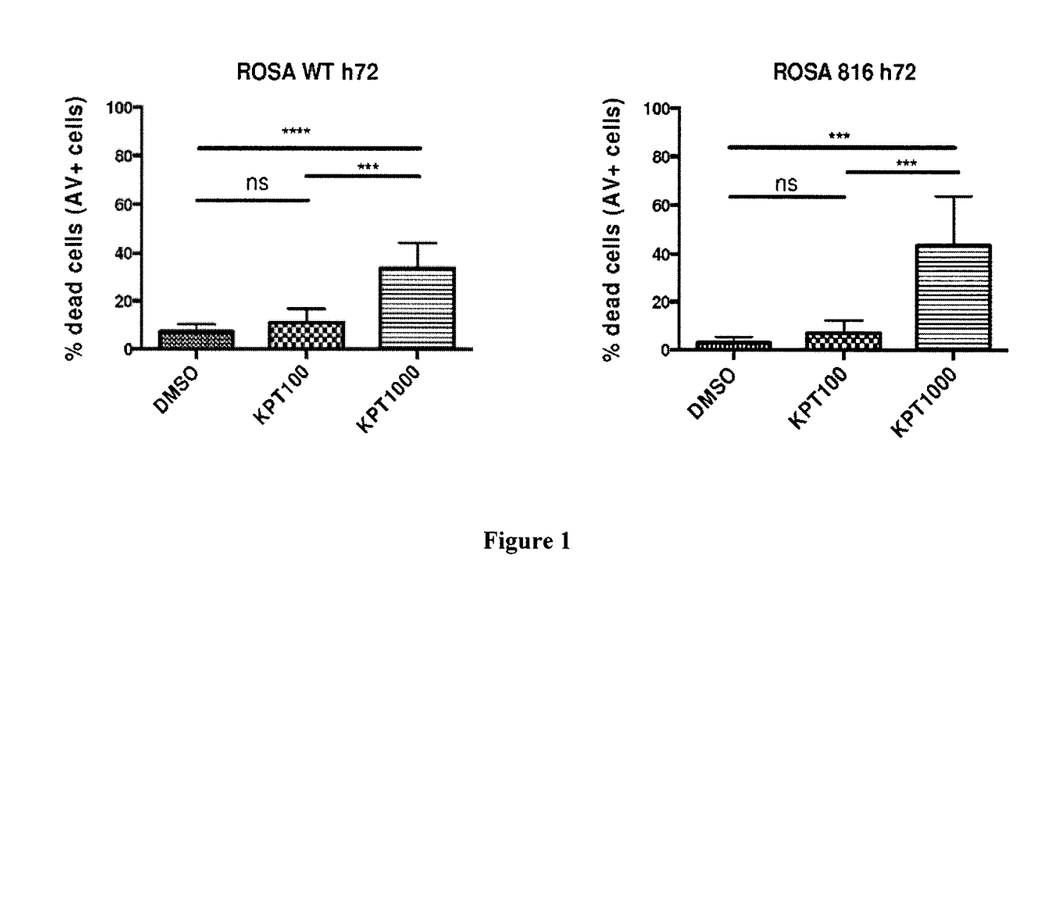
FIG. 1. KPT-251 treatment for 72 hours induces cell death and decreases proliferation in ROSA MC lines. Upper panel: Cell death data are presented in histograms as mean percentage of annexin positive cells ±SD after 72 hours of treatment with KPT at 100 nM, 1000 nM or with DMSO (control) in ROSA WT and ROSA D816V MC lines, n=6 independent experiments. P values are determined by ANOVA Tukeys multiple comparison test. Lower panel: Proliferation curves analysis ±SD of ROSA WT and ROSA D816V MC lines assessed by counting after blue trypan staining at 24, 48 and 72 hours of treatment with KPT at 100 nM, 1000 nM, or with DMSO (control), n=3 independent experiments. P values are determined by one-way ANOVA test, *P<0.05, *P<0,001, **P<0,0001, ns=not significant.
Figure 2:
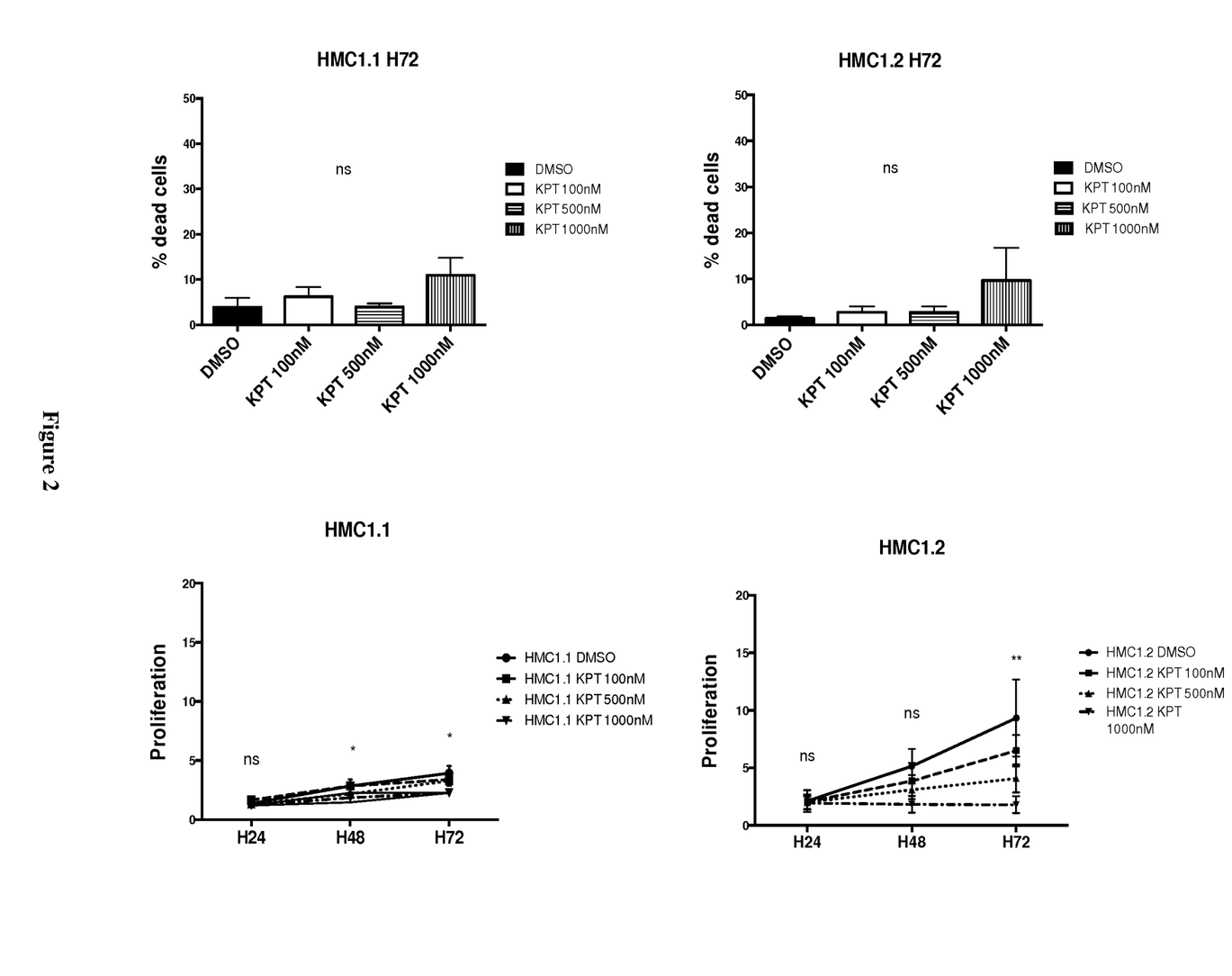
FIG. 2. KPT-251 treatment for 72 hours decreases proliferation in HMC1 MC lines but has no effect on cell death. Upper panel: Cell death data are presented in histograms as mean percentage of dead cells ±SD assessed by counting after blue trypan staining after 72 hours of treatment with KPT at 100 nM, 500 nM, 1000 nM or DMSO (control) in HMC1.1 and HMC1.2 MC lines, n=3 independent experiments. P values are determined by ANOVA Tukeys multiple comparison test. Lower panel: Proliferation curves analysis ±SD of HMC1.1 and HMC1.2 MC lines assessed by blue trypan staining at 24, 48 and 72 hours of treatment with KPT100 nM, 500 nM, KPT1000 nM, or DMSO (control), n=3 independent experiments. P values are determined by one-way ANOVA test, *P<0.05, **P<0,01, ns=not significant.

We show that a 72 hours treatment with KPT 251 induces a significant dose dependent increase in cell death and a decrease in cell proliferation in ROSA cell lines, independently of KIT mutation. We show that a 72 hours treatment with KPT 251 has a weak effect on cell death in HMC1.1 and HMC1.2 cells but significatively decreases proliferation in a dose dependent manner, more importantly in HMC1.2 cell line.

Figure 3:
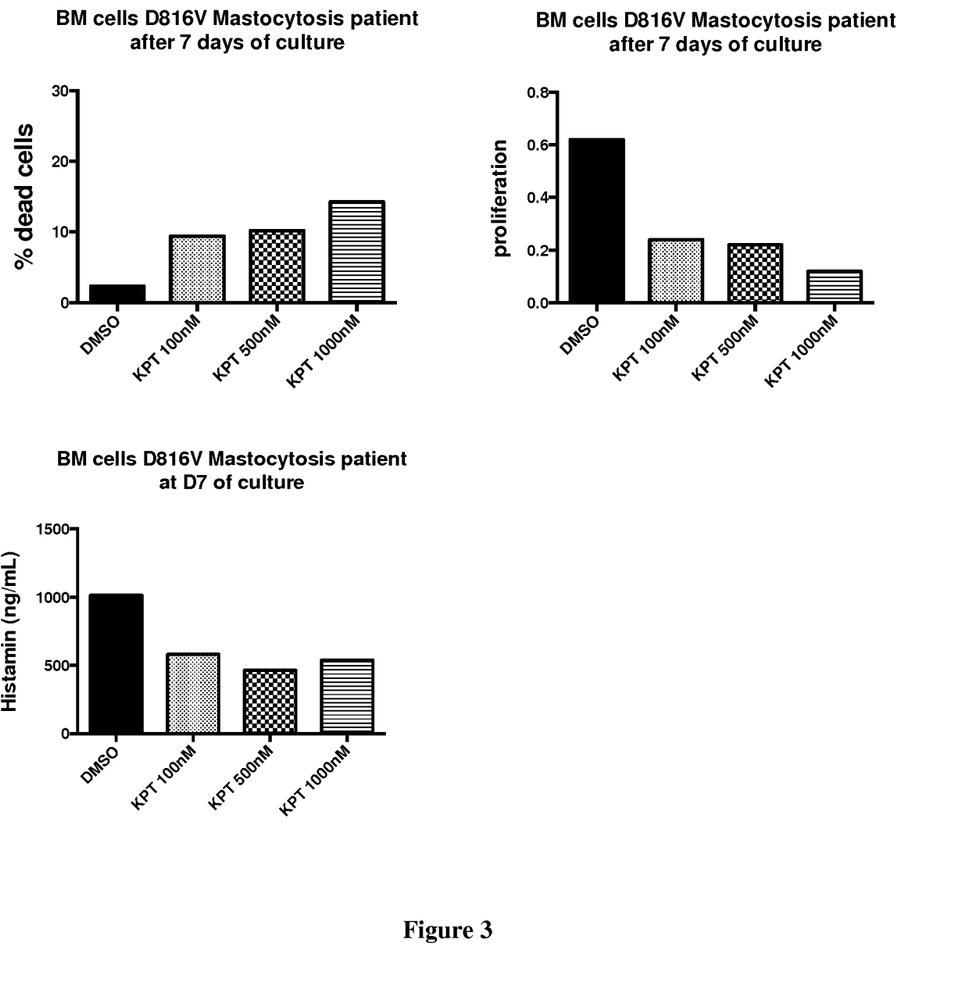
FIG. 3. KPT-251 treatment for 7 days induces cell death and decreases proliferation in bone marrow cells from a patient with aggressive mastocytosis with D816V mutation, and decreases the secretion of histamin in culture media. Upper panel: Cell death data presented as percentage of dead cells, and proliferation data, are presented in histograms. Cell death and proliferation were assessed by counting after blue trypan staining, after 7 days of treatment with KPT at 100 nM, 500 nM, 1000 nM or DMSO (control), n=1. Lower panel Histamin concentration in ng/mL was quantified in cell culture media of bone marrow cells from the patient, after 7 days of treatment with KPT at 100 nM, 500 nM, 1000 nM or DMSO (control), n=1

Finally, in bone marrow cells from the patient, KPT induced a decrease in proliferation, an increase in cell death and a decrease in media concentration of histamine compared to control (DMSO). Histamin is a mediator secreted by mastocytes, responsible for disturbing MC activation symptoms in patients like flushing, pruritus, and urticarial.

In the light of our results, KPT constitutes a promising candidate for the treatment of SM, more precisely the three categories of advanced SM: SM with an Associated clonal Hematologic Non-MC lineage Disease (SM-AHNMD), Aggressive SM (ASM) and Mast Cell Leukemia (MCL) that are associated with a poor prognosis and lack effective treatment options. More interestingly, KPT is efficient in SM with D816V mutation of KIT which represents a major fraction of SM.

KPT is currently studied in clinical trials for the treatment of myeloma, AML, advanced hematological cancer, MDS and other cancer types. Importantly, clinical studies have already shown promising results of selinexor (KPT-330), in phase 1 and 2 for the treatment of AML (NCT01607892, NCT02088541, NCT02249091, NCT02403310, NCT02093403, NCT02485535, NCT02299518, NCT02416908, NCT02212561, NCT01607892 and NCT02091245) and MDS (NCT02212561). Indeed, used alone or in combination with conventional therapies, it is active in inducing remission in patients with relapsed or refractory AML. Furthermore, KPT has no significant effect on normal hematopoietic stem and progenitor cells.

As it offers a rationale for treatment with cytotoxicity against myeloid neoplasms, KPT might thus confer a double therapeutic advantage in advanced SM (SM-AHNMD, ASM and MCL) that are frequently associated with second hematologic process such as myeloproliferative neoplasm (MPN). Second generation KPT-8602 has effective activity against AML blasts and leukemia-initiating cells with better tolerance compared to first generation KPT thanks to a reduced brain penetration."

REFERENCES

Throughout this application, various references describe the state of the art to which this invention pertains. The disclosures of these references are hereby incorporated by reference into the present disclosure.

Savona M, Garzon R, de Nully Brown P, Yee K, Lancet J E, Gutierrez M et al. Phase I Trial of Selinexor (KPT-330), a first-in-class oral Selective Inhibitor of Nuclear Export (SINE) in patients (pts) with advanced acute myelogenous leukemia (AML). 58th ASH Annual Meeting & Exposition, New Orleans, LA, USA, December 7-10, 2013.

Rubnitz J, Kaufman R, Ribeiro R C, Klebanov B, Ellis J, Landesman Y et al Phase I study of Selinexor, a selective inhibitor of nuclear export, in combination with Fludarabine and Cytarabine in pediatric patients with relapsed or refractory AML. In: ASH Annual Meeting, Orlando, Fla., USA, December 2015.

Fiedler W, Chromik J, Kebenko M, Thol F, Trummer A, Schünemann C et al Selinexor, ARA-C and Idarubicin: an effective and tolerable combination in patients with relapsed/refractory AML: a multicenter phase II study. In: ASH Annual Meeting, Orlando, Fal., USA, December 2015.

Chen C, Garzon R, Gutierrez M, Jacoby M A, Brown P, Flinn I W et al Safety, efficacy, and determination of the recommended phase 2 dose for the oral Selective Inhibitor of Nuclear Export (SINE) Selinexor (KPT-330). In: ASH Annual Meeting, Orlando, Fla., USA, December 2015.

[i] Etchin et al., «Antileukemic Activity of Nuclear Export Inhibitors That Spare Normal Hematopoietic Cells »; Lapalombella et al., «Selective Inhibitors of Nuclear Export Show That CRM1/XPO1 Is a Target in Chronic Lymphocytic Leukemia »; Etchin et al., «KPT-330 Inhibitor of CRM1 (XPO1)-Mediated Nuclear Export Has Selective Anti-Leukaemic Activity in Preclinical Models of T-Cell Acute Lymphoblastic Leukaemia and Acute Myeloid Leukaemia »; Kojima et al., «Prognostic Impact and Targeting of CRM1 in Acute Myeloid Leukemia »; Walker et al., «Preclinical and Clinical Efficacy of XPO1/CRM1 Inhibition by the Karyopherin Inhibitor KPT-330 in Ph+ Leukemias ».

[ii] Etchin et al., «KPT-8602, a Second-Generation Inhibitor of XPO1-Mediated Nuclear Export, Is Well Tolerated and Highly Active against AML Blasts and Leukemia-Initiating Cells ».

The invention claimed is:

1. A method of treating systemic mastocytosis in a patient in need thereof comprising administering to the patient a therapeutically effective amount of a XPO1 inhibitor, wherein the XPO1 inhibitor is KPT-330, KPT-276, or KPT-251.

2. The method of claim 1 wherein the XPO1 inhibitor is KPT-330.

3. The method of claim 1 wherein the XPO1 inhibitor is KPT-276.

4. The method of claim 1 wherein the XPO1 inhibitor is KPT-251.

* * * * *